United States Patent
Patel et al.

(10) Patent No.: US 6,175,033 B1
(45) Date of Patent: Jan. 16, 2001

(54) METHOD AND CATALYST SYSTEM FOR PRODUCING AROMATIC CARBONATES

(75) Inventors: Ben Purushotam Patel, Albany; Grigorii Lev Soloveichik, Latham; Donald Wayne Whisenhunt, Jr., Niskayuna; Kirill Vladimirovich Shalyaev, Clifton Park, all of NY (US)

(73) Assignee: General Electric Company, Schenectady, NY (US)

( * ) Notice: Under 35 U.S.C. 154(b), the term of this patent shall be extended for 0 days.

(21) Appl. No.: 09/510,381

(22) Filed: Feb. 22, 2000

(51) Int. Cl.$^7$ .................................................. C07C 68/00
(52) U.S. Cl. .................. 558/274; 558/271; 558/272; 558/273; 502/324
(58) Field of Search ................................................ 558/274

(56) References Cited

U.S. PATENT DOCUMENTS

| | | |
|---|---|---|
| 4,187,242 | 2/1980 | Chalk . |
| 5,231,210 | 7/1993 | Joyce et al. . |
| 5,239,106 | 8/1993 | Shafer . |
| 5,284,964 | 2/1994 | Pressman et al. . |
| 5,373,083 | 12/1994 | King et al. . |
| 5,380,907 | 1/1995 | Mizukami et al. . |
| 5,399,734 | 3/1995 | King et al. . |
| 5,498,789 | 3/1996 | Takagi et al. . |
| 5,502,232 | 3/1996 | Buysch et al. . |
| 5,543,547 | 8/1996 | Iwane et al. . |
| 5,726,340 | 3/1998 | Takagi et al. . |
| 5,760,272 | 6/1998 | Pressman et al. . |
| 5,821,377 | 10/1998 | Buysch et al. . |
| 5,856,554 | 1/1999 | Buysch et al. . |

FOREIGN PATENT DOCUMENTS

| | | |
|---|---|---|
| 736325 | 3/1996 | (DE) . |
| 10158221 | 6/1980 | (JP) . |
| 6-271506 | 9/1994 | (JP) . |
| 6-271509 | 9/1994 | (JP) . |
| 7-145107 | 6/1995 | (JP) . |
| 8-89810 | 4/1996 | (JP) . |
| 8-92168 | 4/1996 | (JP) . |
| 8-193056 | 7/1996 | (JP) . |
| 9-110804 | 4/1997 | (JP) . |
| 9-255629 | 9/1997 | (JP) . |
| 9-278715 | 10/1997 | (JP) . |
| 9-278716 | 10/1997 | (JP) . |

*Primary Examiner*—Michael G. Ambrose
(74) *Attorney, Agent, or Firm*—Noreen C. Johnson; Douglas E. Stoner

(57) ABSTRACT

A method and catalyst system for producing aromatic carbonates from aromatic hydroxy compounds. In one embodiment, the method includes the step of contacting at least one aromatic hydroxy compound with oxygen and carbon monoxide in the presence of a carbonylation catalyst system having an effective amount of a manganese source in the absence of a Group VIII B metal source. In various alternative embodiments, the carbonylation catalyst system can include at least one inorganic co-catalyst, as well as a halide composition and/or a base.

13 Claims, 1 Drawing Sheet

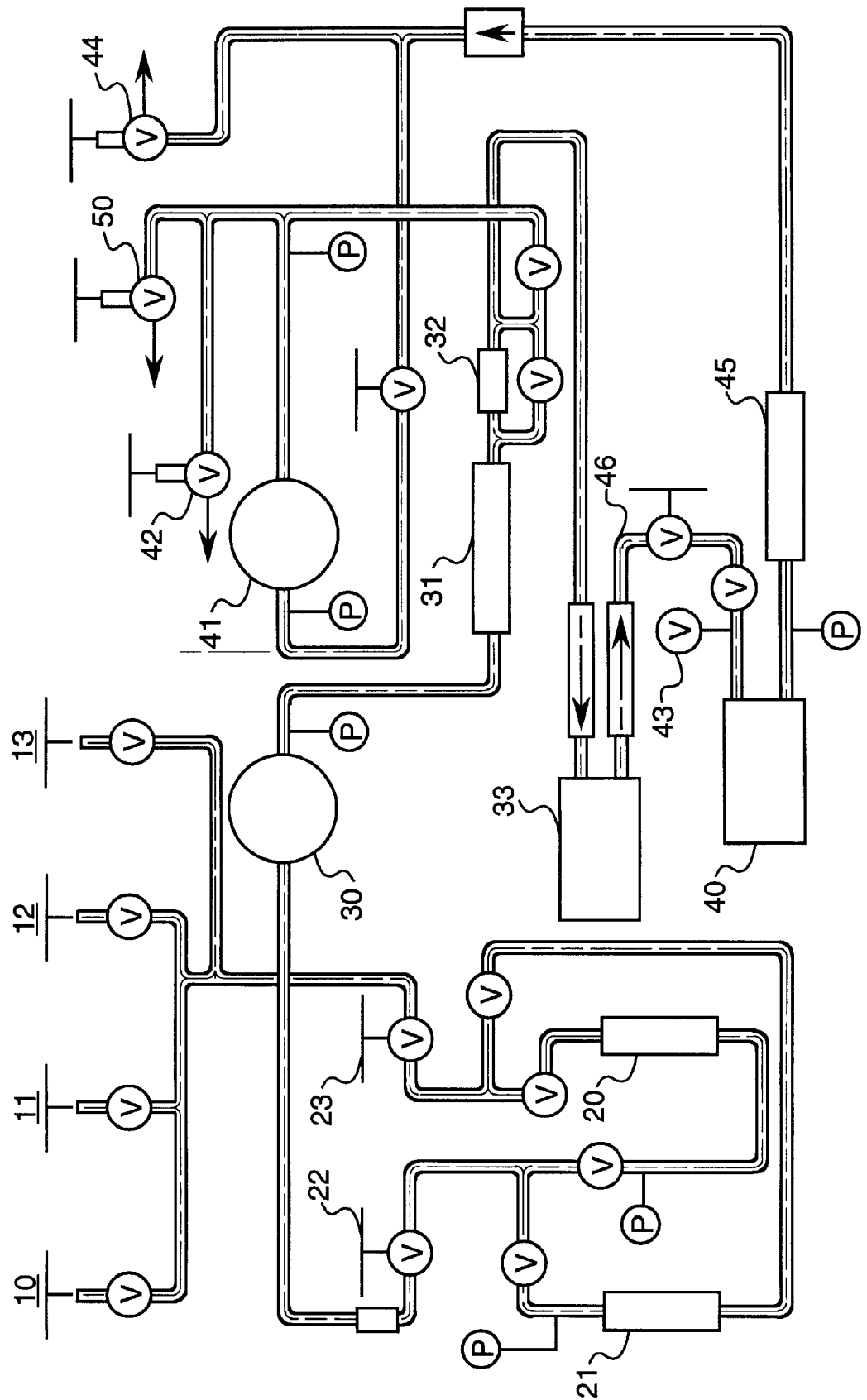

METHOD AND CATALYST SYSTEM FOR PRODUCING AROMATIC CARBONATES

BACKGROUND

1. Field of the Invention

The present invention is directed to a method and catalyst system for producing aromatic carbonates and, more specifically, to a method and catalyst system for producing diaryl carbonates through the carbonylation of aromatic hydroxy compounds.

2. Discussion of Related Art

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group VIII B metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

Unfortunately, due to the significant expense of using a Group VIII B metal as the primary catalyst in a bulk process, the economics of the aforementioned carbonylation systems is strongly dependent on the number of moles of aromatic carbonate produced per mole of Group VIII B metal utilized (i.e. "catalyst turnover"). Consequently, much work has been directed to the identification of efficacious co-catalyst combinations that increase primary catalyst turnover. For example, in U.S. Pat. No. 5,231,210, which is also assigned to the present assignee, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system.

Until the work underlying the teachings of the present disclosure, however, few or no resources have been dedicated to identifying effective substitutes for the Group VIII B metal (typically palladium) as the primary catalyst in the carbonylation reaction. Given the recent, substantial increases in the cost of palladium, even substitutes exhibiting comparatively low activity can be economically viable.

Unfortunately, the literature is not instructive regarding the role of many catalyst components in the carbonylation reaction (i.e. the reaction mechanism), and meaningful guidance regarding the identification of effective combinations of catalyst system components is cursory at best. Accordingly, due to the lack of guidance in the literature, the identification of effective carbonylation catalyst systems has become a serendipitous exercise.

As the demand for high performance plastics has continued to grow, new and improved methods of providing product more economically are needed to supply the market. In this context, various processes and catalyst systems are constantly being evaluated; however, the identities of additional economically effective catalyst systems for these processes continue to elude the industry. Consequently, a long felt, yet unsatisfied need exists for economically superior methods and catalyst systems for producing aromatic carbonates and the like.

SUMMARY OF THE INVENTION

Accordingly, the present invention is directed to a method and catalyst system for producing aromatic carbonates. In one embodiment, the method includes the step of contacting at least one aromatic hydroxy compound with oxygen and carbon monoxide in the presence of a carbonylation catalyst system having an effective amount of a manganese source in the absence of an effective amount of a Group VIII B metal source.

In various alternative embodiments, the carbonylation catalyst system can include catalytic amounts of at least one inorganic co-catalyst, as well as effective amounts of a halide composition and/or a base.

BRIEF DESCRIPTION OF THE DRAWING

Various features, aspects, and advantages of the present invention will become more apparent with reference to the following description, appended claims, and accompanying drawing, wherein the FIGURE is a schematic view of a device capable of performing an aspect of an embodiment of the present invention.

DETAILED DESCRIPTION OF PREFERRED EMBODIMENTS

The present invention is directed to a method and catalyst system for producing aromatic carbonates. In one embodiment, the method includes the step of contacting at least one aromatic hydroxy compound with oxygen and carbon monoxide in the presence of a carbonylation catalyst system having an effective amount of a manganese source in the absence of an effective amount of a Group VIII B metal source.

For convenience, the constituents of the catalyst system described herein are called "components" irrespective of whether a reaction between specific components actually occurs either before or during the carbonylation reaction. Therefore, the catalyst system may include the components and any reaction products thereof.

Unless otherwise noted, the term "effective amount" as used herein includes that amount of a component capable of either increasing (directly or indirectly) the yield of the carbonylation product or increasing selectivity toward an aromatic carbonate. Optimum amounts of a given component can vary based on reaction conditions and the identity of other components, yet can be readily determined in light of the discrete circumstances of a given application.

Aromatic hydroxy compounds which may be used in the present process include aromatic mono or polyhydroxy compounds, such as phenol, cresol, xylenol, resorcinol, hydroquinone, and bisphenol A. Aromatic organic mono hydroxy compounds are preferred, with phenol being more preferred.

The carbonylation catalyst system contains an effective amount of a manganese source as the primary catalyst component. Suitable manganese sources include manganese halides, nitrates, carboxylates, oxides and manganese complexes containing carbon monoxide, amines, phosphines or olefins. As used herein, the term "complex" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes. In various applications, it may be preferable to utilize manganese salts of organic acids, including carboxylates with $C_{2-6}$ aliphatic acids. Suitable manganese sources include manganese (II or III) acetylacetonate, as well as methylcyclopentadienyl manganese tricarbonyl, manganese (II) cyclohexanebutyrate, and bis (3,5-t-busalicylidene) cyclohexanediamino manganese (III) chloride.

The manganese source may be a non-supported manganese salt or complex. As used herein, the term "non-supported" indicates the absence of industrially conventional catalyst supports based on carbon, element oxides, element carbides or element salts in various presentations. Examples of supports containing carbon are coke, graphite, carbon black and activated carbon. Examples of element oxide catalyst supports are $SiO_2$ (natural or synthetic silicas, quartz), $Al_2O_3$ ($\alpha$-, $\gamma$- $Al_2O_3$), aluminas, natural and synthetic aluminosilicates (zeolites), $TiO_2$ (rutile, anatase), $ZrO_2$ and ZnO. Examples of element carbides and salts are SiC, $AlPO_4$, $BaSO_4$, and $CaCO_3$.

The present manganese based catalyst system does not require a component chosen from the Group VIII B metals (i.e., Ru, Pt, Pd, Rh, Os, Ir) or a compound thereof. Surprisingly, the presently disclosed catalyst system effectively catalyzes the carbonylation reaction in the absence of a costly Group VIII B metal source, thereby effectively insulting the process from the volatile market for these elements.

In various alternative embodiments, the carbonylation catalyst system can include a catalytic amount of at least one inorganic co-catalyst (IOCC). It has been discovered that IOCC's and combinations of IOCC's can effectively catalyze the carbonylation reaction in the presence of the aforementioned manganese-based catalyst system. Such IOCC's and combinations include copper, lead, copper and zirconium, and titanium and cerium. Additional IOCC's may be used in the carbonylation catalyst system, provided the additional IOCC does not deactivate (i.e. "poison") the original IOCC combination.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present system. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components. An IOCC may be used in its elemental form if sufficient reactive surface area can be provided. It may be preferable that an IOCC is non-supported as discussed above relative to the manganese source.

IOCC's are included in the carbonylation catalyst system in catalytic amounts. In this context a "catalytic amount" is an amount of IOCC (or combination of IOCC's) that increases the number of moles of aromatic carbonate produced per mole of manganese utilized; increases the number of moles of aromatic carbonate produced per mole of halide composition utilized; or increases selectivity toward aromatic carbonate production beyond that obtained in the absence of the IOCC (or combination of IOCC's). Optimum amounts of an IOCC in a given application will depend on various factors, such as the identity of reactants and reaction conditions. For example, when copper is utilized as an IOCC in the reaction, the molar ratio of copper relative to manganese at the initiation of the reaction is preferably between about 1 and about 100.

The carbonylation catalyst system may further contain an effective amount of a halide composition, such as an organic halide salt. In various preferred embodiments, the halide composition can be an organic bromide or chloride salt. The salt may be a quaternary ammonium or phosphonium salt, such as tetraethylammonium bromide, tetrabutylammonium chloride, or the like. To address economic or regulatory concerns, alkali metal or alkaline earth metal salts may be preferable in certain applications. In preferred embodiments, the carbonylation catalyst system can contain between about 5 and about 2000 moles of halide per mole of manganese employed, and, more preferably, between about 50 and about 1000 molar equivalents of halide are used.

The carbonylation catalyst system can also include an effective amount of a base. Any desired bases or mixtures thereof, whether organic or inorganic may be used. A non-exclusive listing of suitable inorganic bases include alkali metal hydroxides and carbonates; $C_2$–$C_{12}$ carboxylates or other salts of weak acids; and various alkali metal salts of aromatic hydroxy compounds, such as alkali metal phenolates. Hydrates of alkali metal phenolates may also be used. Examples of suitable organic bases include tertiary amines and the like. Preferably, the base used is an alkali metal salt incorporating an aromatic hydroxy compound, more preferably an alkali metal salt incorporating the aromatic hydroxy compound to be carbonylated to produce the aromatic carbonate. Suitable bases include sodium phenoxide and sodium hydroxide. In preferred embodiments, between about 5 and about 1000 molar equivalents of base are employed (relative to manganese), and, more preferably, between about 50 and about 700 molar equivalents of base are used.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide or a combination of at least one inert gas and carbon monoxide and, in any event, outside the explosion range for safety reasons. It is contemplated that oxygen can be supplied in diatomic form or from another oxygen containing source, such as peroxides and the like. Additional gases may be present in amounts that do not deleteriously affect the carbonylation reaction. The gases may be introduced separately or as a mixture. A total pressure in the range of between about 10 and about 250 atmospheres is preferred. Drying agents, typically molecular sieves, may be present in the reaction vessel. Reaction temperatures in the range of between about 60° C. and about 150° C. are preferred. Gas sparging or mixing can be used to aid the reaction.

In order that those skilled in the art will be better able to practice the present invention reference is made to the FIGURE, which shows an example of a continuous reactor system for producing aromatic carbonates. The symbol "V" indicates a valve and the symbol "P" indicates a pressure gauge.

The system includes a carbon monoxide gas inlet 10, an oxygen inlet 11, a manifold vent 12, and an inlet 13 for a gas, such as carbon dioxide. A reaction mixture can be fed into a low pressure reservoir 20, or a high pressure reservoir 21, which can be operated at a higher pressure than the reactor for the duration of the reaction. The system further includes a reservoir outlet 22 and a reservoir inlet 23. The gas feed pressure can be adjusted to a value greater than the desired reactor pressure with a pressure regulator 30. The gas can be purified in a scrubber 31 and then fed into a mass flow controller 32 to regulate flow rates. The reactor feed gas can be heated in a heat exchanger 33 having appropriate conduit prior to being introduced to a reaction vessel 40. The reaction vessel pressure can be controlled by a back pressure regulator 41. After passing through a condenser 25, the reactor gas effluent may be either sampled for further analysis at valve 42 or vented to the atmosphere at valve 50. The reactor liquid can be sampled at valve 43. An additional valve 44 can provide further system control, but is typically closed during the gas flow reaction.

In the practice of one embodiment of the invention, the carbonylation catalyst system and aromatic hydroxy compound are charged to the reactor system. The system is sealed. Carbon monoxide and oxygen are introduced into an appropriate reservoir until a preferred pressure (as previously defined) is achieved. Circulation of condenser water is initiated, and the temperature of the heat exchanger 33 (e.g., oil bath) can be raised to a desired operating temperature. A conduit 46 between heat exchanger 33 and reaction vessel 40 can be heated to maintain the desired operating temperature. The pressure in reaction vessel 40 can be controlled by the combination of reducing pressure regulator 30 and back pressure regulator 41. Upon reaching the desired reactor temperature, aliquots can be taken to monitor the reaction.

EXAMPLES

The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner. Unless otherwise specified, all parts are by weight, and all equivalents are relative to manganese. Reaction products were verified by gas chromatography. Unless otherwise noted, all reactions were carried out in a glass, batch reactor at 100° C. in an approximately 6–9% $O_2$ in CO atmosphere. The glass reactor was sealed with a semi-permeable membrane and placed in an autoclave containing the reaction atmosphere at a pressure of approximately 110 atmosphere (i.e., negligible pressure differential across the walls of the glass reaction vessel). Reaction time was 3 hours for each run.

In the following examples, the aromatic carbonate produced is diphenylcarbonate (DPC). For convenience, the number of moles of DPC produced per mole of manganese utilized is referred to as the manganese turnover number (Mn TON).

Example 1

Diphenyl carbonate was produced by adding, at ambient conditions, a substantially homogeneous catalyst system containing 1 mM manganese (II) acetylacetonate ("Mn (acac)$_2$"), 5 equivalents of copper in the form of copper (II) acetylacetonate ("Cu(acac)$_2$"), and 100 equivalents of bromide in the form of tetraethylammonium bromide ("TEAB") to a glass reaction vessel containing phenol. The components were heated to 100° C. for 3 hours in an approximately 7.8 % oxygen in carbon monoxide atmosphere at approximately 110 atm. total pressure. The following results were observed:

| Experiment No. | Mn(acac)$_2$ mM | Cu(acac)$_2$ Equivalents | TEAB Equivalents | Mn TON |
|---|---|---|---|---|
| 1 | 1 | 5 | 100 | 4 |
| 2 | 1 | 5 | 100 | 6 |

The data show that a Mn TON at least as high as 6 can be obtained utilizing this catalyst system. Based on the results of these experiments, it is evident that a catalyst system containing Mn, Cu, and an onium bromide can effectively catalyze the carbonylation reaction.

Example 2

The general procedure of Example 1 was repeated with various manganese sources such as manganese (II) cyclohexanebutyrate ("Mn(CyButyrate)$_2$") and Bis (3,5-t-Busalicylidene)cyclohexanediamino manganese (III) chloride ("(Mn(salen*)Cl"). Experimental runs were carried out with and without a halide composition and with Cu(acac)2 as well as lead oxide to produce the following results:

| Experiment No. | Mn source 1 mM | Cu(acac)$_2$ Equivalents | PbO Equivalents | TEAB Equiv. | Mn TON |
|---|---|---|---|---|---|
| 1 | Mn(CyButyrate)$_2$ | 5 | — | 100 | 4 |
| 2 | Mn(CyButyrate)$_2$ | 5 | — | 100 | 2 |
| 3 | Mn(salen*)Cl | 5 | — | 100 | 4 |
| 4 | Mn(acac)$_2$ | — | 10 | 100 | 3 |
| 5 | Mn(CyButyrate)$_2$ | — | 10 | 100 | 9 |
| 6 | Mn(acac)$_2$ | — | — | — | 7 |
| 7 | Mn(CyButyrate)$_2$ | — | — | — | 7 |

The results show that various combinations of Mn, IOCC, and onium halide can effectively catalyze the carbonylation reaction.

Example 3

The general procedure of Examples 1 and 2 was repeated with 1 mM of varios manganese sources 5 equivalents of Cu(acac)$_2$, and TEAB or ammonium chloride ("TBAC"). Reactions were carried out in a 7.8% carbon monoxide atmosphere at approximately 56 atm. total pressure. The results were observed:

| Experiment No. | Mn source 1 mM | Cu(acac)2 Equivalents | TBAC Equiv. | TEAB Equiv. | Mn TON |
|---|---|---|---|---|---|
| 1 | Mn(CyButyrate)$_2$ | 5 | — | 100 | 2 |
| 2 | Mn(CyButyrate)$_2$ | 5 | — | 100 | 3 |
| 3 | Mn(salen*)Cl | 5 | — | 100 | 2 |
| 4 | Mn(acac)$_2$ | 5 | 100 | — | 5 |
| 5 | Mn(CyButyrate)$_2$ | 5 | 100 | — | 4 |
| 6 | Mn(acac)$_2$ | 5 | 100 | — | 4 |
| 7 | Mn(CyButyrate)$_2$ | 5 | 100 | — | 4 |

The results show that various combinations of Mn, IOCC, and onium halide can effectively catalyze the carbonylation reaction at lower pressures.

Example 4

The general procedure of Examples 1–3 was repeated with 1 mM Mn(acac)$_2$, 50 equivalents of TEAB, and the following IOCC combination: 2 equivalents of Cu(acac)$_2$ and 5 equivalents of zirconium in the form of zirconium (IV) butoxide ("Zr(OBu)$_4$"). The Mn TON was found to be 6, thus showing that the combination of Mn, Cu, Zr, and onium bromide can effectively catalyze the carbonylation reaction.

Example 5

The general procedure of Examples 1–4 was repeated with 1 mM Mn(acac)$_2$, 50 equivalents of TEAB, 50 equivalents of sodium hydroxide, and the following IOCC combination: 5 equivalents of titanium and 2 equivalents of cerium. Titanium was provided as titanium (IV) oxide acetylacetonate ("TiO(acac)$_2$") and cerium as cerium (III) acetylacetonate ("Ce(acac)$_3$"). The Mn TON was found to be 2, thus showing that the combination of Mn, Ti, Ce, onium bromide, and base can effectively catalyze the carbonylation reaction.

Example 6

The general procedure of Examples 1–5 was repeated with manganese methylcyclopentadienyl manganese tricarbonyl ("Cp*Mn(CO)$_3$"), TEAB, and either Cu(acac)$_2$ or PbO at approximately 107 atm. to produce the following results:

| Experiment No. | CP*Mn(CO)$_3$ | Cu(acac)2 Equivalents | PbO Equivalents | TEAB Equiv. | Mn TON |
|---|---|---|---|---|---|
| 1 | 1 | 5 | — | 75 | 2 |
| 2 | 1 | — | 5 | 75 | 4 |
| 3 | 1 | — | 5 | 75 | 4 |
| 4 | 1 | — | 5 | 75 | 5 |

The results show that various combinations of Mn, IOCC, and onium bromide can effectively catalyze the carbonylation reaction.

It will be understood that each of the elements described above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method of carbonylating an aromatic hydroxy compound, said method comprising the step of contacting at least one aromatic hydroxy compound with oxygen and carbon monoxide in the presence of a carbonylation catalyst system comprising an effective amount of a manganese source as a primary catalyst component, and wherein said method is carried out in the absence of an effective amount of a Group VIII B metal source.

2. The method of claim 1, wherein the carbonylation catalyst system further comprises a catalytic amount of an inorganic co-catalyst.

3. The method of claim 2, wherein the inorganic co-catalyst is a copper source.

4. The method of claim 2, wherein the inorganic co-catalyst is a lead source.

5. The method of claim 1, wherein the carbonylation catalyst system further comprises a combination of inorganic co-catalysts.

6. The method of claim 5, wherein the combination of inorganic co-catalysts comprises a catalytic amount of a copper source and a catalytic amount of a zirconium source.

7. The method of claim 5, wherein the combination of inorganic co-catalysts comprises a catalytic amount of a titanium source and a catalytic amount of a cerium source.

8. The method of claim 1, wherein the carbonylation catalyst system further comprises an effective amount of a halide composition.

9. The method of claim 8, wherein the halide composition is tetraethylammonium bromide.

10. The method of claim 8, wherein the halide composition is tetrabutylammonium chloride.

11. The method of claim 1, wherein the aromatic hydroxy compound is phenol.

12. The method of claim 2, wherein the carbonylation catalyst system further comprises an effective amount of a base.

13. A method of carbonylating an aromatic hydroxy compound, said method comprising the step of:
    contacting at least one aromatic hydroxy compound with oxygen and carbon monoxide in the presence of a carbonylation catalyst system comprising the following components:
        an effective amount of a manganese source as a primary catalyst component, and wherein said method is carried out in the absence of an effective amount of a Group VIII B metal source;
        a catalytic amount of an inorganic co-catalyst; and
        an effective amount of a halide composition.

* * * * *